United States Patent [19]

Katzenellenbogen

[11] 4,064,150

[45] Dec. 20, 1977

[54] SYNTHESIS OF ISOPRENOID 1,5-DIENES

[75] Inventor: John A. Katzenellenbogen, Urbana, Ill.

[73] Assignee: University of Illinois Foundation, Urbana, Ill.

[21] Appl. No.: 690,090

[22] Filed: May 26, 1976

[51] Int. Cl.$^2$ .................. C11C 1/00; C07C 53/00
[52] U.S. Cl. ...................... 260/413; 260/526 N; 260/514 L; 252/522
[58] Field of Search .......... 260/413 R, 413 K, 413 L, 260/413 S, 526 N, 631.5, 489, 486 R, 514 L; 252/522

[56] References Cited

U.S. PATENT DOCUMENTS 3,971,827  7/1976  Baran et al. .................. 260/526 N

OTHER PUBLICATIONS

Katzenellenbogen, J., Journal of the American Chemical Society, vol. 96, pp. 5662-5663, (1974).

*Primary Examiner*—Winston A. Douglas
*Assistant Examiner*—John F. Niebling
*Attorney, Agent, or Firm*—Mathew L. Kalinowski

[57] ABSTRACT

Aliphatic acids containing an isoprenoid 1,5-diene moiety are prepared in high yields by the selective gamma alkylation of $\alpha,\beta$-unsaturated acids with allylic electrophiles. The gamma-regioselectivity of the alkylation is controlled by the use of the dicopper(I) dienolates prepared from the $\alpha,\beta$-unsaturated acids. The method offers a particularly facile means for synthesizing isoprenoid 1,5-diene natural products such as farnesoic acid by alkylation of senecioic acid with geranyl bromide; geranoic acid by alkylation of senecioic acid with 3,3-dimethallyl bromide; and dl-lanceol by alkylation of tiglic acid with an allylic bromide derived from dl-limonene. Such products find use in the synthesis of insect pheremones, insect juvenile hormones, and components of perfumes.

18 Claims, No Drawings

SYNTHESIS OF ISOPRENOID 1,5-DIENES

The invention described herein was made in the course of work under a grant from the Department of Health, Education, and Welfare, and the Government has rights in this invention pursuant to Grant No. MPS-73-08691 awarded by the National Science Foundation.

BACKGROUND OF THE INVENTION

This invention relates to novel aliphatic acids containing isoprenoid 1,5-diene structural units and to a method for preparing them. More particularly this invention relates to the preparation of such acids by the selective gamma-alkylation of a dicopper(I) dienolate of an aliphatic α,β-unsaturated acid with an allylic electrophile.

The alkylation of aliphatic α,β-unsaturated carbonyl compounds at the gamma position would appear to be a convenient route for the synthesis of compounds containing isoprenoid 1,5-diene units which compounds are important in many biological systems and natural products. This approach is severely limited, however, because all reported alkylations occur largely at the alpha carbon atom ("Molecular Rearrangements", P. de Mayo, Ed., Interscience, New York, New York, 1963, p. 345). For example, in the case of an α,β-unsaturated ester, it has been shown that the lithium enolate formed by treatment of ethyl trans-3-methyl-2-hexenoate with lithium diisopropylamide in tetrahydrofuran undergoes alkylation with allyl bromide predominately at the alpha position and produces the isomeric alpha- and gamma-alkylation products in a 95:5 ratio.

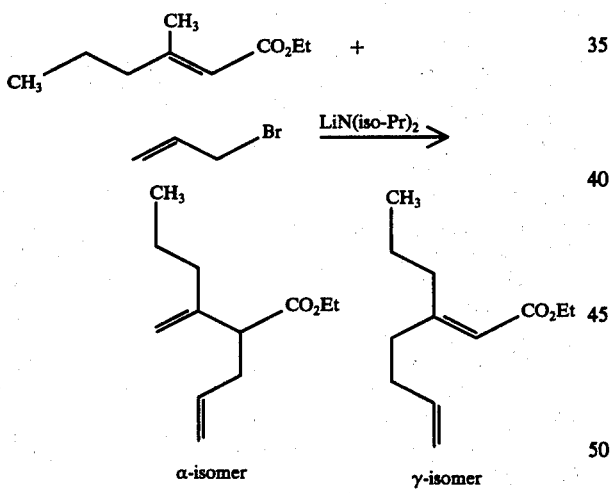

More desirable results were obtained with the copper enolate, which was found to give a 44:56 ratio of alpha to gamma products (J. A. Katzenellenbogen et al., J. Amer. Chem. Soc., 96, 5662(1974)).

Other investigators have reported the alkylation of the lithium enolate of ethyl crotonate with methyl iodide yielded less than 5% of the gamma isomer (J. L. Herrman et al., Tetrahedron Lett., 2433(1973)). Somewhat better gamma-regioselectivity was obtained, 60:40 alpha- to gamma-alkylation, when crotonic acid was alkylated with methyl iodide (P. E. Pfeffer et al., Tetrahedron Lett., 1163(1973)).

A method for selective gamma-alkylation of α,β-unsaturated carbonyl compounds in the synthesis of compounds containing isoprenoid 1,5-diene units is highly desirable because alkylation at the gamma site preserves both the structure of the carbon skeleton (isoprene polymer) and the pattern of oxygen functionality (at chain termini) as they are found most often in natural products. Such a structural and functional pattern can be advantageously employed in the synthesis of insect pheremones, insect juvenile hormones, and components of perfumes.

SUMMARY OF THE INVENTION

This invention is directed to the synthesis of novel aliphatic acids containing 1,5-isoprenoid diene moieties by the steps including forming a dicopper (I) dienolate of an aliphatic α,β-unsaturated acid and selectively alkylating the dienolate at the gamma position with an allylic electrophile. The corresponding sodium, potassium, magnesium, manganese, cobalt and iron enolates were found to be much less effective in the synthesis.

Suitable α,β-unsaturated acids are the acrylic acids having the formula:

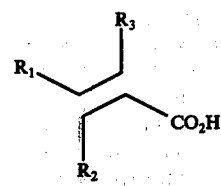

where $R_1$, $R_2$, and $R_3$ can be hydrogen or a $C_1 - C_5$ aliphatic group.

Particularly suitable α,β-unsaturated acids are shown in Scheme 1.

SCHEME 1

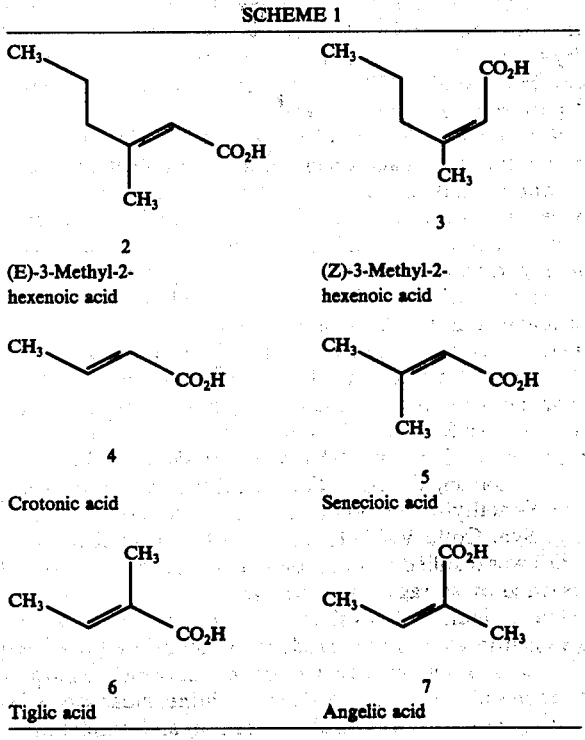

2
(E)-3-Methyl-2-hexenoic acid 3
(Z)-3-Methyl-2-hexenoic acid

4
Crotonic acid

5
Senecioic acid

6
Tiglic acid

7
Angelic acid

Suitable allylic electrophiles have the formula:

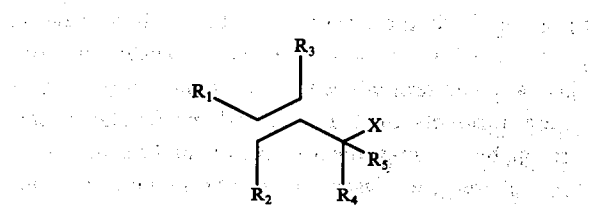

where $X$ is a halide or sulfonate and $R_1$, $R_2$, $R_3$, $R_4$, and $R_5$ are hydrogen or $C_1 - C_{12}$ aliphatic or cycloaliphatic groups.

Particularly suitable allylic electrophiles are such allylic halides as allyl bromide, 3,3-dimethallyl bromide, trans-1-bromo-2-methyl-2-butene, 2-methyl-2-propenyl chloride, geranyl bromide and 2-(1'-methylcyclohexen-4'-yl)-2-propenyl bromide and allylic sulfonates as 2-methyl-1-buten-3-yl methanesulfonate and 2-methyl-1-hepten-3-yl methane sulfonate.

PREFERRED EMBODIMENTS OF THE INVENTION

General — Analytical gas-liquid phase chromatography (glpc) was performed on the Hewlett-Packard, Model 5750, gas chromatograph with a flame ionization detector, using a carrier gas (nitrogen) flow of 30 ml/min. The following columns were used for analytical work: A, 0.125 in. × 10 ft., 5% SE-30 on Gas-Chrom Q; B, 0.125 in. × 5 ft., 3% OV-17 on Gas-Chrom Q. Preparative glpc was done on the Varian Aerograph gas chromatograph, Model 90-P3 with a thermal conductivity detector, using helium as a carrier gas. Two columns were used: C, 0.375 in. × 12 ft., 15% SE-30 on Chromosorb W, and D, 0.375 in. × 5 ft., 15% Carbowax on Chromosorb W. Where glpc analysis was employed, compounds are listed in order of increasing retention time on the column specified.

The proton magnetic resonance (pmr) spectra were determined on Varian A-60A and HA-100 spectrometers. The chemical shifts are expressed as delta ($\delta$) values (parts per million downfield from internal tetramethylsilane). Infrared (ir) data was obtained using PerkinElmer Model 137 spectrometer, and the data are expressed in units of frequency (cm$^{-1}$).

Solvents and Commercial Chemicals — The supplier of n-butyl lithium and phenyllithium was Ventron Corporation. Methanesulfonyl chloride, triethyl phosphonacetate, dllimonene, 2-pentanone, triphenylmethane, allyl alcohol, tiglic acid, propargyl alcohol, senecioic acid, geraniol, and crotonic acid were purchased from Aldrich. Matheson, Coleman, and Bell supplied allyl bromide and triethylamine. Crotyl bromide and dimethylallyl bromide came from the Chemical Samples Company, and isocrotyl chloride and phosphorous tribromide were from Eastman Company. Cuprous iodide from Fisher Scientific Company was used without further purification. Eu(TFN)$_3$ was from Kary Laboratories (Anderson, S. C.). Diazomethane was prepared from N-methyl-N-nitrourea by the procedure of Arndt (Org. Syn. Coll., Vol. II, 165(1943)). Tetrahydrofuran (THF) was distilled from sodium naphthalide, and ether was dried by storage over sodium.

Unless indicated otherwise, all reactions were quenched in water and products isolated in a standard fashion: extraction with an organic solvent, washing extract with aqueous solutions (e.g. brine, bicarbonate), drying with anhydrous salts, filtration, and removal of solvent under vacuum by rotary evaporation. In each case the solvents etc. used in the procedure are given in parentheses. The letter (E) in a compound refers to cis configuration; the letter (Z) to trans configuration. Compound numbers and letters shown in parentheses or underlined refer to structures shown in Scheme 1 and Table I.

Ethyl (E)-3-Methyl-2-hexenoate and Ethyl (Z)-3-Methyl-2-hexenoate To a suspension of 6.0 g (0.24 mol) of NaH in THF at 25° under $N_2$, was added 56.0 g (0.25 mol) of triethyl phosphonoacetate in 50 ml THF. After stirring 1 hour, 22 g (0.256 mol) of 2-pentanone was added, and the reaction stirred overnight. The THF was removed via distillation, and the residue poured into water, extracted with two portions of ether, washed twice with equal volumes of saturated NaCl solution, and dried over MgSO$_4$. According to glpc analysis, a 4:1 mixture of trans to cis isomers was obtained. Solvent was removed in vacuo, and the residue distilled on a Nester-Faust teflon annular spinning band column. Second spinning band distillation of cis enriched fractions was required to obtain the pure cis ester. Ethyl (E)-3-Methyl-2-hexenoate: pmr (CDCl$_3$) $\delta$5.6 ($m$,1), 4.1 ($q$,2), 2.3–1.9 ($m$,2), 2.2 ($s$,3), 1.7–1.2 ($m$,2), and 0.95 ($t$,3).

Anal. Calcd. for C$_9$H$_{16}$O$_2$: C 69.19; H, 10.32. Found, 69.15; H, 10.28.

Ethyl (Z)-3-Methyl-2-hexenoate: pmr (CDCl$_3$) $\delta$ 5.6 ($m$,1), 4.1 ($q$,2), 2.6 ($t$,2), 1.9 ($d$,3), 1.8–1.2 ($m$,2), 1.23 ($t$,3), and 0.95 ($t$,3).

(E)-3-Methyl-2-hexenoic Acid(2) — In a flask containing 30 ml of 20% KOH and 5 ml of EtOH was added 6.8 g (0.044 mol) of ethyl (E)-3-methyl-2-hexenoate. This mixture was refluxed over steam for one hour and poured into 20 ml of ice water. Product isolation (Et$_2$O, brine, MgSO$_4$) gave the above acid which crystallized upon cooling. Recrystallization from ethanol-water gave 5.1 g (89%) of the above acid: mp39°–40°; pmr (CCl$_4$) $\delta$ 10.57 ($s$,1), 5.67 ($s$,1), 2.1 ($s$,3), 2.2–2.0 ($m$,2), 1.8–1.1 ($m$,2), and 0.90 ($t$,3).

(Z)-3-Methyl-2-hexenoic Acid(3) — Hydrolysis of ethyl (Z)-3-methyl-2-hexenoate by the above procedure gave an oil that was shown to be an 85:15 mixture of cis and trans isomers by glpc analysis (Col. A, 120°) after methylation with diazomethane.

(E)-2-Methyl-2-butenyl Bromide (C) — Using an excess of diazomethane in ether, 4 g (0.04 mol) of tiglic acid dissolved in a minimum of Et$_2$O, was methylated. After the solution had turned from yellow to clear, the ester was obtained quantitatively (MgSO$_4$) and used without further purification: pmr (CDCl$_3$)$\delta$6.85 ($m$, 1), 3.65 ($s$,3), 1.82 ($s$,3), and 1.77 ($d$,3).

To a slurry of 1.38 g (0.036 mol) of LiAl H$_4$ in 30 ml of anhydrous Et$_2$O at 0° under N$_2$, was added 1.6 g (0.012 mol) of AlCl$_3$. After stirring 30 min at 25° and cooling to 0°, 2.6 g of methyl tiglate (0.228 mol) in 5 ml of Et$_2$O was added slowly via syringe. The mixture stirred 1 hr. at 25° and was quenched with 1 ml of H$_2$O, followed by 1 ml of 15% KOH, and 3 ml of H$_2$O. Product isolation (sat. aqueous NaHCO$_3$, brine, MgSO$_4$) and distillation (bp 122°–127°) gave 1.33 g (68%) of (E)-2-methyl-2-buten-1-Ol: pmr (CCl$_4$) $\delta$ 6.8 ($m$,1), 3.8 (br $s$,1), 3.65 ($s$,2), 1.80 ($s$,3), and 1.73 ($d$,3); ir (neat) 3350 (O—H), 2900 (C—H), 1670 (C=C), 1450 (C=C), and 1050 (C—O) cm$^{-1}$.

The above alcohol was converted to the bromide, C, by placing 1.3 g (0.155 mol) in a flask with 20 ml of anhydrous Et$_2$O at 0° under N$_2$ in the absence of light. Using a syringe, 1.62 g (0.006 mol) of PBr$_3$ was added slowly, and the reaction stirred at 0° for 2 hr. Product isolation (ice water, Et$_2$O, brine, MgSO$_4$) gave 1.82 g oc C (74%): ir (neat) 2900 (C—H), 1670 (C=C), and 1450 (C=C) cm$^{-1}$.

2-Methyl-1-buten-3-yl Methanesulfonate (D) — Methyllithium (0.1 mol) was added to a flask containing 50 ml of anhydrous Et$_2$O at 0° under N$_2$. Then 7 g (0.1 mol) of methacrolein in 10 ml Et$_2$O was added slowly via dropping funnel. After 1 hr., the reaction was quenched by addition of 20 ml of water. Product isolation (Et$_2$O, brine, MgSO$_4$) gave 6 g (69%) of 2-methyl-buten-3-ol (bp 110°–113°): pmr (CCl$_4$) δ 4.8 (d,2), 4.1 (m,1), 4.05 (s,1), 1.8 (s,3), and 1.2 (d,3); ir (neat) 3400 (O—H), 2900 (C—H), 1650 (C=C), and 1050 (C—O) cm$^{-1}$.

This alcohol (3 g, 0.035 mol) was placed in a flask containing 3.63 g (0.036 mol) of triethylamine and 30 ml of CH$_2$Cl$_2$ under N$_2$ at 0°. While stirring, 4.10 g (0.036 mol) of methanesulfonyl chloride was added dropwise. After another 15 min., the reaction was poured into ice water. Product isolation (Et$_2$O, 5% HCl, sat. aqueous NaHCO$_3$, brine, MgSO$_4$) gave 3.2 g (66%) of D that was used without further purification, since it easily decomposed: ir (neat) 2900 (C—H), 1650 (C=C), 1350 (S=O), and 1170 (S=O) cm$^{-1}$.

2-Methyl-1-hepten-3-yl Methanesulfonate (E) — To a flask containing 0.35 mol of n-butyllithium in 100 ml of ether at 0° under N$_2$, was added, dropwise, 24 g (0.35 mol) of methacrolein in 25 ml of ether. The reaction stirred 2 hr. at 0° and was quenched by careful addition of water. Product isolation (Et$_2$O, brine, MgSO$_4$) gave 23 g (72%) of crude 2-methyl-1-hepten-3ol that was purified further by chromatography on silica gel. The alcohol (16 g, 15%) eluted with ether-hexane (35:65): pmr (CDCl$_3$) δ 4.83 (d,2), 4.0 (m,1), 3.1 (br s,1), 1.7 (s,3), and 1.6–0.8 (m,9); ir (neat) 3300 (O—H), 2900 (C—H), 1650 (C=C), and 1050 (C—O) cm$^{-1}$.

This alcohol (2.5 g, 0.0295 mol) was added to a flask with 20 ml of CH$_2$Cl$_2$ and 2.02 g (0.02 mol) of triethylamine. After flushing the flask with N$_2$ and reducing the temperature to 0°, 2.28 g (0.02 mol) of methanesulfonyl chloride was added slowly. After 1 hr. at 0°, the mixture was poured into ice water. Product isolation (Et$_2$O, sat. aqueous NaHCO$_3$, MgSO$_4$) gave an oil that was not further purified as it decomposed readily: ir (neat) 2900 (C—H), 1650 (C=C), 1350 (S=O), and 1180 (S=O) cm$^{-1}$.

General Method for Dilithium Dienolate Formation From Unsaturated Acids (2–4,5,7). (Method I) — To a 2.02 g (0.020 mol) of diisopropylamine in 25 ml THF under nitrogen at −78°, was added n-butyllithium (0.020 mol). The pale yellow solution was stirred about 10 min., and 0.01 mol of the desired acid, dissolved in 10–15 ml THF, was added slowly. This stirred 30 min. at 0°, forming a clear yellow solution.

General Method for Lithium-Sodium Dienolate Formation From Unsaturated Acids. (Method II) — The sodium salt of the acid to be alkylated was formed by adding dropwise 0.01 mol of the acid in 5 ml of THF to a slurry of NaH (0.012 mol) in 15 ml of THF under nitrogen at 0°. This was heated over a steam bath for 10 min or until formation of a thick white mixture. While this was heating, one equiv. of lithium diisopropylamide was generated by adding 0.010 mol of n-buthyllithium to a flask containing 1.01 g (0.010 mol) of diisopropylamine in 20 ml THF under nitrogen atmosphere at −78°.

The thick white slurry was cooled to 0°, and the lithium amide solution (at −78°) was slowly siphoned into this mixture while rapidly stirring, preferably using an overhead stirrer. Stirring was continued at 0° for 15 min. then at 25° until dianion formation was complete. This is indicated by a clear (or translucent if running a large scale reaction) yellow solution. If a white collodial solution persists, after stirring at 25° for more than 30 min., the salt of the acid has probably precipitated to some extent, and complete dianion generation will be impossible. Should this occur, it is best to abort the run and to repeat the process taking care (1) not to overheat the sodium salt of the acid, (2) to use a fresh bottle of n-butyllithium, (3) to maintain rapid stirring of the sodium salt of the acid while lithium diisopropylamide is being siphoned in, and (4) to add the lithium diisopropylamide slowly.

General Method for Alkylation of Acid Dilithium of Lithium Sodium Dienolates. (Method A) — The acid dienolate is formed by Method I or II, depending on the acid, and the appropriate allylic halide (1–3 equiv.) is added dropwise to the acid dienolate at 0° under nitrogen atmosphere. There should be a color change from yellow to colorless. This mixture is stirred at 25° for 1 hr. and quenched.

General Method for Alkylation of Acid Dicopper Dienolate. (Method B) — After the dienolate of the acid (0.010 mol) is generated via the appropriate method (I or II), the solution is cooled to −78°. Maintaining a nitrogen atmosphere, 3.89 g (0.020 mol) of cuprous iodide is added, and the slurry is stirred rapidly at −78° for 1 hour. The copper dienolate is formed successfully if the slurry is pale to bright yellow in color. If it is a pale greyish white, the lithium (or lithium-sodium) dienolate predominates, and if it is black, the dienolate has decomposed, and subsequent γ-selective alkylation will be impossible. The halide is added at −78° and stirring is continued overnight (16 hr.), during which time the reaction mixture warms to 25°.

Acid Product Isolation 1 — If the acid product was C$_{10}$ or less, the reaction was quenched with H$_2$O, stirred, and filtered through Celite. Sodium hydroxide solution was added to pH 12, causing more copper salts to precipitate; these were removed by filtration through Celite. The mixture was then extracted with two equal volumes of ether to remove the non-acidic organic residues. The combined aqueous layers were acidified to pH 3 (acid to congo red paper), and were extracted with two equal volumes of Et$_2$O. These extracts were washed with brine and dried over MgSO$_4$, and the product acid was obtained after removal of the solvent under vacuum.

Acid Product Isolation 2 — An acid of C$_{11}$–C$_{14}$ was isolated by quenching the reaction with 5% HCl, acidifying with 6N HCl to below pH 3 and filtering through Celite. The acid product was obtained by extracting with ether, drying the extracts with brine and MgSO$_4$, and removing the solvent under vacuum.

Acid Product Isolation 3 — The cleanest work-up involved product acids of C$_{15}$ or more. Dilute HCl (3%) was added to quench the alkylation, and saturated NH$_4$Cl solution was added until all of the copper salts were dissolved. The product was removed via extraction with ether. Salt (NaCl) was added to the blue NH$_4$Cl layer, and any residual acid product was extracted with more ether. The combined extracts were dried (brine, MgSO$_4$) and evaporated to give the acid product.

Alpha-Alkylation of (E)-3-Methyl-2-hexenoic Acid (2) with Allyl Bromide (A). (Method A) — Acid 2 (0.05 mol) was alkylated with 1.01 g (0.01 mol) of allyl bromide (A) by generating the lithium-sodium dienolate (Method II) and alkylating via Method A. After isolation 1, the crude acid was methylated with excess diazomethane producing 0.70 g (83%) of an oil. Glpc analysis (Col. A, 140°) showed two peaks, A and B, in ratio 98:2. Peak A (retention time of 6.4 min.) was isolated on preparative glpc (Col. C) and assigned the structure of the α-allylated product methyl 2-(1'-penten-2'-yl)-4-pentenoate: pmr (CCl$_4$) γ 5.9–5.4 (m,l), 5.1–4.8 (overlapping doublets,4), 3.56 (s,3), 2.95 (s,1), 2.6–2.2 (m,2), 2.0 (t,2), 1.65–1.3 (m,2), and 0.9 (t,3).

Anal. Calcd. for $C_{11}H_{18}O_2$: C, 72.49; H, 9.95. Found: C, 72.13; H, 9.73.

Peak B had the same retention time (10.3 min.) as the γ-allylated product which was synthesized in Method B (following procedure).

Gamma-Alkylation of 2 with Allyl Bromide (Method B) — The lithium-sodium dienolate of 2 (1.28 g, 0.01 mol) was generated according to Method II cuprous iodide (3.89 g, 0.02 mol) was added according to alkylation B to form the copper dienolate for subsequent alkylation with 2.00 g (0.02 mol) af allyl bromide. After isolation and methylation (with diazomethane), 1.5 g (82%) of product was obtained. Glpc analysis (Col. A, 140°) showed two product peaks, A and B, in the ratio 19.4:80.6. Peak A (retention time of 6.4 min.) was identified as the α-allylated product by pmr analysis (see preceeding procedure, Method A). Peak B (retention time of 10.3 min.) was isolated by preparative glpc (Col. C) and assigned the structure of the γ-allylated product, methyl 3-propyl-2,6-heptadienoate: pmr (CCl$_4$) δ 6–5.6 (m,1), 5.54 (s,1), 5.1–4.8 (overlapping doublets, 2), 5.58 (s,3), 2.66 (t,2), 2.3–2.0 (m,4), 1.65–1.4 (m,2), and 0.9 (t,3).

Anal. Calcd. for $C_{11}H_{18}O_2$: C, 72.49; H, 9.95. Found: C, 71.99; H, 9.89.

Alpha-Alkylation of Crotonic Acid (4) with Allyl Bromide (A), (Method A) — The lithium dienolate of 4 was generated via Method I using 0.43 g (0.05 mol) of crotonic acid in 3 ml of THF and 1.01 g (0.01 mol) of diisopropyl amine and 0.01 mol n-butyllithium in 20 ml THF. This dienolate was alkylated with 2.8 g (0.02 mol) of allyl bromide using alkylation A and isolated as outlined in isolation 1. The crude acid was methylated with diazomethane, yielding 0.65 g (90%) of ester. Glpc analysis (Col. A, 120°) showed a major product, 98% (retention time of 2.9 min.), which was isolated via preparative glpc (Col. C) and identified as the α-allylated product, methyl 2-vinyl-4-pentenoate: pmr (CCl$_4$) δ 7–6.8 (m,2), 5.8–5.6 (m,2), 5.2–4.9 (m,2), 3.65 (s,3), 2.95 (m,1), and 2.25 (m,2).

The minor product (2%, retention time of 6 min.), was later identified by glpc comparison as the γ-allylated isomer (see Method B, below).

Gamma-Alkylation of Crotonic Acid (4) with Allyl Bromide, (Method B) — Method I was used to form 0.005 mol of the lithium dienolate of crotonic acid as described above. Addition of cuprous iodide and alkylation with 2.8 g (0.02 mol) of allyl bromide was done according to alkylation Method B. Isolation 1 gave a yellow oil that was methylated with diazomethane, yielding 0.69 g (97%) of ester. Glpc analysis (Col. A, 120°) indicated two peaks, A and B, in the ratio of 3:97. The minor product (retention time of 2.9 min.) was shown to be the α-allylated product by glpc comparison with the major product of the preceeding reaction (Method A above). The major product in this case (retention time of 6 min.) was isolated by preparative glpc (Col. C) and shown to be the γ-allylated product, methyl (E)-2,6-heptadienoate: pmr (CCl$_4$) δ 6.9–6.7 (m,1), 5.9–5.6 (m,2), 3.65 (s,3), and 2.24 (m,4).

Anal. Calcd for $C_8H_{12}O_2$: C, 68.50; H, 8.58. Found: C, 68.21; H, 8.75.

Alpha-Alkylation of Senecioic Acid (5) with Allyl Bromide (A), (Method A) — The lithium-sodium dianion of senecioic acid (1 g, 0.01 mol) was generated via Method II with 0.43 g (0.01 mol) of NaH and 0.01 mol of lithium diisopropylamide. Excess allyl bromide (2.02 g, 0.022 mol) was added according to alkylation Method A. Using isolation 1 and diazomethane methylation, 1.43 g (93%) of ester was obtained as a yellow oil. Glpc analysis (Col. A, 115°) indicated two peaks, A and B, in the ratio 95.5:4.5. Peak A was isolated by preparative glpc (Col. C) and shown by pmr to be the α-allylated product, methyl 2-isopropenyl-4-pentenoate: pmr (CCl$_4$) δ 5.9–5.4 (m,1), 5.1–4.9 (overlapping doublets,2), 4.85 (d,2), 3.62 (s,3), 3.01 (t,1), 2.7–2.1 (m,2), and 1.7 (d,J=0.5 Hz,3).

Anal. Calcd for $C_9H_{14}O_2$: C, 70.10; H, 9.15. Found: C, 70.19; H, 9.02.

Peak B was assigned as the cis gamma product by glpc comparison with the products from the following reactions (Method B).

Gamma-Alkylation of Senecioic Acid (5) with Allyl Bromide (A), (Method B) — The dianion generation from 1 g (0.01 mol) of senecioic acid was repeated (Method II), and 3.89 g (0.02 mol) of cuprous iodide was added. Subsequently, alkylation with 2.02 g (0.022 mol) of allyl bromide according to alkylation Method B, and isolation 1, gave an oil that was methylated with diazomethane. The yield was determined to be 89.5% (glpc with internal standard), and by glpc (Col. A, 115°), three peaks, A, B, and C, were evident in the ratio 7.2:46:47. All three were isolated by preparative glpc (Col. C). Peak A was identical with the α-allylated product whose preparation is described in the preceeding procedure (Method A). Peaks B and C are the γ-cis and γ-transallylated products, respectively. Peak B, (methyl (Z)-3-methyl-2,6-heptadienoate): pmr (CCl$_4$) δ 5.9–5.6 (m,1), 5.57 (s,1), 5.1–4.8 (overlapping doublets,2), 3.65 (s,3), 2.68 (t,2), 2.2 (m,2) and 1.84 (d,J=0.5 Hz,3).

Anal. Calcd. for $C_9H_{14}O_2$: C, 70.10; H, 9.15. Found: C, 70.00; H, 9.12 Peak C, (methyl (E)-3-methyl-2,6-heptadienoate): pmr (CCl$_4$) δ 5.9–5.6 (m,1), 5.57 (s,1), 5.1–4.8 (overlapping doublets,2), 3.65 (s,3), 2.2 (d,4), and 2.1 (d, J=0.5 Hz, 3).

Anal. Calcd. for $C_9H_{14}O_2$: C, 70.10; H, 9.15. Found: C, 69.97; H, 9.10.

Alpha-Alkylation of Tiglic Acid (6) with Allyl Bromide (A), (Method A) — The lithium dienolate of 0.5 g (0.005 mol) of tiglic acid was generated with 1.01 g (0.01 mol) of diisopropylamine and 0.01 mol n-butyllithium as in Method I. The dienolate was then alkylated with 1.4 g (0.011 mol) of allyl bromide according to alkylation A and isolated according to 1. After methylation with diazomethane, a yellow oil (0.705 g, (90%) gave one peak on glpc (Col. A, 105°), which was shown to be the α-allylated product, methyl 2-methyl-2-vinyl-4-pentenoate: pmr (CDCl$_3$) δ 6.07 (d of d, J$_1$ = 17 Hz and J$_2$ = 10 Hz,1), 5.8–5.45 (m,1), 5.2–4.9 (overlapping doublets,4), 3.65 (s,3), 2.38 (m,2), and 2.24 (s,3).

Anal. Calcd. for $C_9H_{14}O_2$: C, 70.10; H, 9.15. Found: C, 70.19; H, 9.02.

Gamma-Alkylation of Tiglic Acid (6) with Allyl Bromide (A), (Method B) — Using 1.01 g (0.01 mol) of diisopropyl amine, 0.01 mol of n-butyllithium, 25 ml of THF, and 0.5 g (0.005 mol) of tiglic acid, dienolate generation by Method I was performed. The anion was alkylated using Method B with 1.4 g (0.011 mol) of allyl bromide. Isolation 1 was used to give the crude acid. After methylation with diazomethane, the oil was analyzed on glpc (Col. A, 110°), and the yield was determined to be 95% by internal standard (cyclohexylcarboxylic acid was added to the reaction after quenching but before work-up). Two product peaks in a 4:96 ratio were found; the first (retention time 4.8 min.) was the α-allylated product (cf., preceeding procedure, Method A). The second (retention time 11.9 min.) was isolated by preparative glpc (Col. C) and shown to be the trans γ-allylated product, methyl (E)-2-methyl-2,6-heptadienoate: pmr (CDCl$_3$) δ 6.75 (t,1), 6–5.6 (m,1), 5.2–4.9 (overlapping doublets,2), 3.65 (s,3), 2.22 (m,4), and 1.83 (d, J=0.5 Hz,3).

Anal. Calcd. for C$_9$H$_{14}$O$_2$: C, 70.10; H, 9.15. Found: C, 70.25; H, 9.67.

Gamma-Alkylation of Tiglic Acid (6) with Dimethylallyl Bromide (B), (Method B) — The dienolate of tiglic acid (0.5 g, 0.005 mol) was generated using Method I, and alkylation with dimethylallyl bromide (1.92 g, 0.013 mol) proceeded as described in alkylation B. After isolation 2, the crude acid mixture was methylated with diazomethane and analyzed on glpc (Col. B, 140°). Two major product peaks, A (retention time of 3.2 min.) and B (retention time of 5.6 min.) in a ratio of 15:85 were isolated by preparative glpc (Col. C), and identified as the α- and γ-substituted esters. The yield was determined to be 68% via glpc internal standard. Methyl 2,5-dimethyl-2-vinyl-4-hexenoate (α-substituted product): pmr (CCl$_4$) δ 6.07 (d of d, J$_1$=17 Hz and J$_2$=10 Hz,1), 5.06 (d,1), 4.92 (d,2), 3.65 (s,3), 2.25 (m,2), 1.67 (s,3), 1.58 (s,3), and 1.17 (s,3).

Anal. Calcd. for C$_{11}$H$_{18}$O$_2$: C, 72.49; H, 9.95. Found: C, 72.48; H, 9.98.

Methyl (E)-2,7-dimethyl-2,6-octadienoate (δ-substituted product): pmr (CCl$_4$) δ 6.65 (m,1), 5.05 (m,1), 3.65 (s,3), 2.1 (m,4), 1.77 (d, J=0.5 Hz,3), 1.66 (s,3), and 1.58 (s,3).

Anal. Calcd. for C$_{11}$H$_{18}$O$_2$: C, 72.49; H, 9.95. Found: C, 72.01; H, 9.88.

Gamma-Alkylation of Tiglic Acid (6) with (E)-1-Bromo-2-Methyl-2-Butene (C), (Method B) — Tiglic acid (0.5 g, 0.005 mol) was lithiated (dienolate generation I), complexed with 1.89 g (0.01 mol) of cuprous iodide, and alkylated with 0.5 g (0.003 mol) of C via alkylation B. After isolation 2, the crude acids were methylated with diazomethane, yielding 0.45 g (78%) of the methyl esters. There were two products via glpc (Col. B, 125°) in the ratio 65.6:34.4, A (retention time of 2.4 min.) to B (retention time of 3.6 min.). The products were isolated on preparative glpc (Col. D) and both shown to be γ-alkylation products: A was methyl (E)-2,5,6-trimethyl-2,6-heptadienoate (9) derived from S$_n$2′ attack, and B was methyl (E,E)-2,6-dimethyl-2,6-octadienoate (8) from S$_n$2 attack.

Peak A, methyl (E)-2,5,6-trimethyl-2,6-heptadienoate (substitution with transposition): pmr (CCl$_4$) δ 6.59 (br t,1), 4.66 (d, J=0.5 Hz,2), 3.63 (s,3), 2.2 (m,3), 1.77 (d, J=0.3 Hz,3), 1.67 (d, J=0.5 Hz, 3), and 1.3 (d, J=6 Hz,3).

Anal. Calcd. for C$_{11}$H$_{18}$O$_2$: C, 72.49; H, 9.95. Found: C, 71.95; H, 9.81

Peak B, methyl (E,E)-2,6-dimethyl-2,6-octadienoate (direct substitution): pmr (CCl$_4$) δ 6.6 (br t,1), 5.2 (br q,1), 3.63 (s,3), 2.3—2.2 (m,4), 1.78 (d, J=0.3 Hz,3), 1.59 (s,3), and 1.56 (d,3).

Anal. Calcd. for C$_{11}$H$_{18}$O$_2$: C, 72.49; H, 9.95. Found: C, 72.42; H, 9.89.

Gamma-Alkylation of Tiglic Acid (6) with 2-Methyl-1-buten-3-yl Methansulfonate (D) (Method B) — Tiglic Acid (0.5 g, 0.005 mol) was metallated (Method I), complexed with 1.89 g of cuprous iodide, and alkylated with 1.5 g (0.009 mol) of D (alkylation B). After isolation 2, the acids were methylated with diazomethane, yielding 0.75 g (78%) of the combined esters. Glpc analysis (Col. B, 110°) showed three products A, B, and C, in the ratio 26:21.5:52.5. The material in peak A was 9 and peak C was 8 (by glpc and pmr comparison). Peak B from this reaction appeared as a shoulder on peak C (8) and was difficult to separate from it by preparative glpc. The pmr spectrum of a mixture of 65% B in C showed only one additional signal, a broad singlet at δ 1.68; thus it appears that the material in peak B is the 6Z isomer of 8: methyl (E,Z)-2,6-dimethyl-2,6-octadienoate.

Gamma-Alkylation of Tiglic Acid (6) with 2-Methyl-1-hepten-3-yl Methanesulfonate (E), (Method B) — Using enolate generation I and alkylation B, the dienolate of 0.5 g (0.005 mol) of tiglic acid was complexed with 1.89 g (0.01 mol) of cuprous iodide and alkylated at −79° with 2.69 g (0.021 mol) of E. After isolation of the crude acids via 3 and methylation with diazomethane, the ester was analyzed on glpc (Col. B, 110°). Since there was only one major product (retention time of 12.2 minutes), the crude product was purified by preparative tlc (ether-hexane 15:85) which gave 0.58 g (55%) of the γ-transposed product, methyl (E,E)-2,6-dimethyl-2,6-undecadienoate, which was further purified on preparative glpc (Col. D): pmr (CCl$_4$) δ 6.62 (br, t,1), 5.1 (br, t,1), 3.64 (s,3), 2.3–2.9 (m,6), 1.79 (d, J=0.3 Hz, 3), 1.60 (d, J=0.5 Hz, 3), 1.4–1.2 (m,4), and 0.9 (t,3).

Anal. Calcd. for C$_{14}$H$_{24}$O$_2$: C, 74.95; H, 10.78. Found: C, 74.40; H, 10.87.

Gamma-Alkylation of Tiglic Acid (6) with 2-Methyl-2-propenyl Chloride (F), (Method B) — The copper dienolate of tiglic acid (0.005 mol) was generated in the usual manner (dienolate generation, Method I, and alkylation B) and alkylated with 0.9 g (0.01 mol) of 2-methyl-2-propenyl chloride. Product was isolated according to 1 and was methylated with excess diazomethane. Glpc analysis (Col. A, 149°) showed two products in the ratio of 4.5:95.5 (A, retention time of 3.2 min; B, retention time of 6 min.) with a combined yield of 87% (glpc with cyclohexylcarboxylic acid as internal standard). The two products were isolated on preparative glpc (Col. C) and identified as the α-substituted ester, methyl 2,4-dimethyl-2-vinyl-4-pentenoate (Peak A): pmr (CCl$_4$) δ 6.08 and 5.89 (doublets, AB pattern, 1), 5.08 (d,2), 4.95–4.6 (overlapping doublets,2), 2.5 (d, J=12 Hz,1), 2.2 (d, J=12 Hz,1), 1.62 (s,3)m and 1.22 (s,3).

The γ-substituted ester, methyl (E)-2,6-dimethyl-2,6-heptadienoate (Peak B): pmr (CCl$_4$) δ 6.62 (t,1), 4.66 (s,2), 3.65 (s,3), 2.16 (m,4), 1.77 (s,3), and 1.70 (s,3).

Anal. Calcd. for C$_{10}$H$_{16}$O$_2$: C, 71.39; H, 9.59. Found: C, 71.48; H, 9.45.

Gamma-Alkylation of Angelic Acid (7) with Allyl Bromide (A), (Method B) — The dienolate of 0.5 g (0.005 mol) of angelic acid was generated with 1.01 g (0.01 mol) of diisopropyl amine and 0.01 mol of n-butyllithium via method I. Alkylation was carried out with 1.4 g (0.011 mol) of allyl bromide as in alkylation B; the reaction was quenched, and the crude acids were isolated by procedure 1 and methylated with diazomethane (0.71 g, 92%). Glpc analysis showed two peaks, A and B, (Col. A, 110°) matching the retention times of the α-(4.8 min.) and γ-allylated (11.9 min.) tiglic esters (vide ante), in the ratio 9.5:90.5. Peak B was isolated on preparative glpc and had a pmr identical to that of the γ-substituted product from the reaction of 6 and A implying that the conjugated double bond in the latter compound was now of the E configuration.

Gamma-Alkylation of Senecioic Acid (5) with Geranyl Bromide, Farnesoic Acids, (Method B) — The copper dienolate from 1 g (0.01 mol) of senecioic acid (5) was formed by initial mixed dienolate generation (Method II) and subsequent addition of 3.89 g (0.02 mol) of cuprous iodide, and 5.0 g (0.025 mol) of geranyl bromide was added as in alkylation B. Isolation by procedure 3 and methylation with diazomethane produced 2.06 g (80%) of a mixture of esters. Using glpc analysis (Col. B, 145°), three major product peaks were found in a ratio of 10:36:54, A (retention time of 4 min.): B (retention time of 6.2 min.): C (retention time of 7.3 min.). Peak A was presumed to be the alpha product, and peaks B and C were identified as the isomeric gamma products by pmr (J. W. K. Burrell et al., J. Chem. Soc., 2144(1966)), after isolation by preparative glpc (Col. D). Methyl (Z,E)-farnesoate (Peak B): pmr (CCl$_4$) δ 5.55 (s,1), 5.1–4.9 (m,2), 3.54 (s,3), 2.58 (t,2), 2.2–1.9 (m,6), 1.82 (d, J=0.5 Hz,3), 1.6 (s,3), and 1.4 (s,6).

Anal. Calcd. for C$_{16}$H$_{26}$O$_2$: C, 76.75; H, 10.47. Found: C, 76.43; H, 10.38.

Methyl (E,E)-farnesoate (Peak C): pmr (CCl$_4$) δ 5.55 (s,1), 5.1–4.9 (m,2), 3.54 (s,3), 2.2–1.9 (m,11), 1.6 (s,3), and 1.4 (s,6).

Anal. Calcd. for C$_{16}$H$_{26}$O$_2$: C, 76.75; H, 10.47. Found: C, 76.97; H, 10.45.

2-(1'-Methylcyclohexen-4'-yl)-2-propen-1-ol — A complex of n-butyllithium tetramethylethylene diamine (TMEDA) was formed by dropwise addition of 8.77 g (0.075 mol) of TMEDA to 0.075 mol n-butyllithium at 25° under an N$_2$ atmosphere. This yellow solution was used to metalate 21 g (0.154 mol) of limonene by dropwise addition of the limonene to the n-BuLi-TMEDA solution at 25°. The dark red reaction mixture was stirred overnight and cooled to below −40°, and dry air was slowly bubbled through taking care to maintain the temperature below −20°. When the exothermic reaction was complete, the vessel was warmed to 25°, and 15 ml of H$_2$O and 70 ml of 25% sodium sulfite solution were added. After vigorous stirring for 24 hours, the layers were separated. Distillation of the product after isolation (Et$_2$O, 5% aqueous HCl, 5% aqueous KOH, brine) gave 3.42 g (30%) of the alcohol containing an aromatic impurity, bp 74°–77° at 0.12 mm (Reported bp 66°–71° at 0.10 mm. R. S. Crawford et al., J. Am. Chem. Soc., 74, 4298(1972)).

Additional purification of the alcohol was done by AgNO$_3$ complexation. A 7.0 g portion of distilled alcohol (combined from two runs) was dissolved in 50 ml of pentane and extracted three times with 20 ml portions of half saturated aqueous AgNO$_3$. The combined AgNO$_3$ fractions were washed with 20 ml of pentane and poured slowly into an equal volume of conc. aqueous NH$_4$OH at 0°. This was extracted twice with 30 ml portions of pentane, which were dried over MgSO$_4$. After solvent removal in vacuo, 2.5 g of alcohol was isolated (35.7%), making the overall isolated yield about 10.7%: pmr (CCl$_4$) δ 5.40 (br s,1), 4.8–5.0 (overlapping doublets,2), 3.98 (s,2), 3.43 (s,1), 2.2–1.85 (m,7), 1.1 (m,2), and 1.62 (s,3); ir (neat) 3300 (O—H), 2900 (C—H), 1650 (C=C), 1430 (C=C), and 1050 (C=O) cm$^{-1}$.

2-(1'-Methylcyclohexen-4'-yl)-2-propenyl Bromide — In a flask containing 60 ml of anhydrous ether and 1.03 g (0.0037 mol) of PBr$_3$ at 0° in the absence of light, was added, dropwise, 2.2 g (0.143 mol) of the alcohol prepared above. After stirring for 2 hr. the reaction was poured into ice water. A 90.5% yield (2.815 g) of the bromide was isolated (Et$_2$O, sat. aqueous NaHCO$_3$, brine, MgSO$_4$): ir (neat) 2900 (C—H), 1650 (C=C), and 1430 (C=C) cm$^{-1}$.

Gamma-Alkylation of Tiglic Acid (6) with 2-(1'-Methylcyclohexen-4'-yl)-2-propenyl Bromide, (Method B) — After forming the copper dienolate of 0.6 g (0.006 mol) of tiglic acid (dienolate Method I, alkylation B), 1.4 g (0.0065 mol) of the above bromide was added slowly. After the reaction was complete, it was quenched with 10 ml of 5% HCl, and isolation procedure 3 was employed. The crude acid was methylated with excess diazomethane, and solvent reduced in vacuo. Only one product peak was seen on glpc (Col. B, 150°). The product was purified by preparative tlc using ether-hexane, (15:85-two developments), which gave 0.63 g (61%) of the ester (A. Manjarrez et al., Tetrahedron, 20, 333(1964)): pmr (CCl$_4$) δ 6.62 (t,1), 5.3 (m,1), 4.72 (d,2), 3.65 (s,3), 2.3–1.85 (m,11), 1.77 (d, J=0.5 Hz,3), and 1.6 (s,3).

dl-Lanceol (A. Manjarrez et al, Tetrahedron, 20, 333(1964); O. P. Vig et al., Indian J. Chem. 5, 475(1967)). — The ester prepared above was reduced to the alcohol using aluminum hydride. Lithium aluminum hydride (0.082 g, 2.1 mmol) was slurried in 15 ml of anhydrous ethyl ether under N$_2$ at 0°, and 0.0939 g (0.7 mol) of aluminum chloride was added. After stirring at 25° for 30 min., the temperature was once more lowered to 0°, and 0.186 g (0.75 mmol) of ester prepared above in 2 ml of ethyl ether was added dropwise with a syringe. After stirring 30 min. at 25°, 0.5 ml of H$_2$O was slowly added, followed by 0.5 ml of 15% KOH, and 1.5 ml of H$_2$O. The heavy white precipitate was removed by filtration and washed with 15 ml of ether. Product isolation (Et$_2$O, brine, MgSO$_4$) and purification by preparative tlc (ether: hexane 30:70-two developments) gave 0.15 g (93.7%) of dl-lanceol: pmr (CDCl$_3$) δ 5.38 (m,2), 4.7 (m,2), 3.96 (s,2), 2.2–1.8 (m,10), and 1.62 (s,6); ir (neat) 3400 (O—H), 2900 (C—H), 1640 (C=C), 1415 (C=C), 1050 (C—O), and 890 (C=C) cm$^{-1}$.

The results from the experiments above are listed in Table I. Data from an earlier study of the alkylation of the corresponding esters are given in parentheses (J. A. Katzenellenbogen et al., Ibid).

TABLE I

REGIOSELECTIVITY, STEREOSELECTIVITY, AND MODE OF SUBSTITUTION IN THE ALKYLATION OF ACID DIENOLATE ANIONS

| Unsaturated System | Alkylating Agent | | Metal | Regioselectivity[a] | | γ-Stereo[b] Selectivity cis/trans | Mode of γ[c] Substitution | Yield[d] % |
|---|---|---|---|---|---|---|---|---|
| | | | | α | γ | | | |
| 2 | A | Br | Li | 98(95) | 2(5) | — | T | 80–83 |
| | | | Cu | 19(45)* | 81(55)* | 81/19 | | |
| | B | Br | Li | 99(95) | 1(5) | — | D | 60–70 |
| | | | Cu | 38(95)* | 62(5)* | 85/15 | | |
| 3[e] | A | Br | Cu | 21* | 79* | 85/15 | T | 70–80 |
| 4 | A | Br | Li | 98 | 2 | — | T | 90 |
| | | | Cu | 3 | 97 | 0/100 | | 97 |
| 5 | A | Br | Li | 96 | 4 | — | T | 93 |
| | | | Cu | 7 | 93 | 50/50 | | (90) |
| | B | Br | Li | 99 | 1 | — | D | 85 |
| | | | Cu | 10 | 90 | 45/55 | | |
| 6 | A | Br | Li | 100(95) | 0(5) | — | T | 80–90 |
| | | | Cu | 4(95) | 96(5) | 0/100 | | (95) |
| | B | Br | Cu | 15* | 85* | 0/100 | D | (68) |
| | C | Br | Cu | 0 | 100* | 0/100 | D-34%* T-66%* | [78] |
| | D | OMs | Cu | 0 | 100* | 0/100 | D-26% T-74% (6Z-79%,6E-21%)[f] | 78 |
| | E | OMs | Cu | 0 | 100* | 0/100 | T(6E>95%)[f] | [55] |
| | F | Cl | Cu | 4* | 96* | 0/100 | — | (87) |
| 7 | A | Br | Cu | 3 | 97 | 0/100 | T | — |

*Denotes new compound
[a]Determined by glpc and pmr analysis of the corresponding methyl esters. See experimental section.
[b]Stereoselectivity refers to geometry about the 2,3-double bond in the γ-alkylated product. Date in parenthesis is for the corresponding esters. See (J. A. Katzenellenbogen et al, Ibid.)
[c]Mode of substitution refers to the attack on the allylic bromide. D = direct (S_N2) and T = transposed (S_N2').
[d]Yields are from the weight of the total isolated acid (base-soluble) fraction. Yields in parenthesis are determined by glpc with an internal standard. Yields in square brackets are of isolated, purified product.
[e]Acid 3 contains ca 15% of 2.
[f]Data in parenthesis refers to the geometry about the 6,7-double bond in the α-alkylated product that originates via allylic transposition.

The data clearly show that lithium enolates of both esters and acids give predominately alpha-alkylated products. The copper(I) dienolates of the esters (results in parentheses) afforded gamma-alkylated products with somewhat better selectivity. In contrast, the dicopper(I) dienolates of the acids yield the gamma-alkylated products with the unexpectedly high selectivity of 62–100%.

The new compounds prepared and indicated in Table I are the following:

1. 2-(1'-penten-2'-yl)-4-pentenoic acid and methyl ester

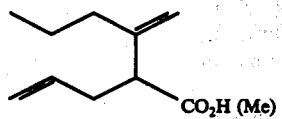

2. 3-propyl-2,6-heptadienoic acid and methyl ester

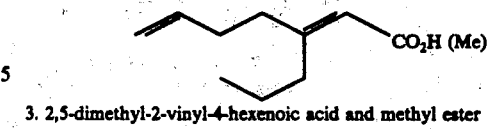

3. 2,5-dimethyl-2-vinyl-4-hexenoic acid and methyl ester

4. (E)-2,5,6-trimethyl-2,6-heptadienoic acid and methyl ester

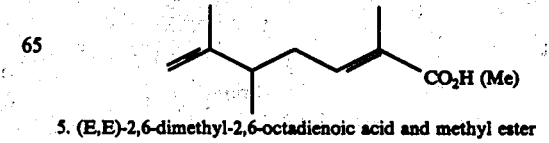

5. (E,E)-2,6-dimethyl-2,6-octadienoic acid and methyl ester

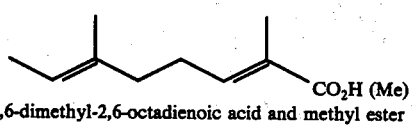
6. (E,Z)-2,6-dimethyl-2,6-octadienoic acid and methyl ester

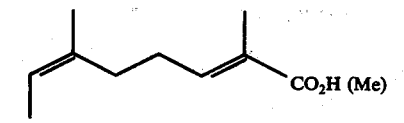
7. (E,E)-2,6-dimethyl-2,6-undecadienoic acid and methyl ester

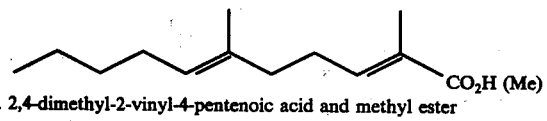
8. 2,4-dimethyl-2-vinyl-4-pentenoic acid and methyl ester

These new compounds are of particular interest as fragrances for the formulation of perfumes, as precursors for the synthesis of insect growth regulators and insect pheromones, as components themselves active as insect growth regulators and pheromones, and as agents with antibacterial and antifungal activity and precursors for the synthesis of other such agents.

I claim:

1. A method of synthesizing aliphatic acids containing 1,5-isoprenoid diene moieties comprising the steps of:
   a. forming a dicopper(I) dienolate of an aliphatic $\alpha,\beta$-unsaturated acid by reaction of the $\alpha,\beta$-unsaturated acid or sodium salt thereof first with lithium dialkyl amide and then with cuprous iodide;
   b. selectively alkylating the dicopper(I) dienolate at the gamma position with an allylic electrophile having the general formula

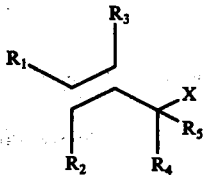

where X = halide or sulfonate and $R_1$–$R_5$ are hydrogen or $C_1$–$C_{10}$ aliphatic or cycloaliphatic groups; and
   c. isolalating the alkylation production from the reaction mixture of step (b).

2. The method of claim 1 wherein the dicopper(I) dienolate of an aliphatic $\alpha,\beta$-unsaturated acid is formed in the steps comprising:
   a. reacting at a temperature of about 0° a molar equivalent of lithium dialkyl amide with a one-half molar equivalent of the aliphatic $\alpha,\beta$-unsaturated acid or one molar equivalent of the sodium salt thereof;
   b. adding at a temperature of about $-80°$ cuprous iodide in the amount of two molar equivalents relative to the dienolate product of step (a); and
   c. maintaining the reaction mixture of step (b) at $-80°$ for 1 hour with rapid stirring.

3. The method of claim 1 wherein the aliphatic $\alpha,\beta$-unsaturated acid has the general formula

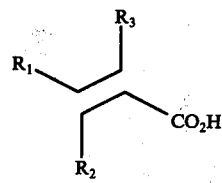

where $R_1$, $R_2$, $R_3$ are hydrogen or a $C_1$–$C_5$ aliphatic group.

4. The method of claim 1 wherein the aliphatic $\alpha,\beta$-unsaturated acid is selected from the group consisting of cis- and trans-3-methyl-2-hexenoic acid, crotonic acid, senecioic acid, tiglic acid and angelic acid.

5. The method of claim 3 wherein the allylic electrophile is selected from the group consisting of allyl bromide, 3,3-dimethallyl bromide, trans-1-bromo-2-methyl-2-butene, 2-methyl-2-propenyl chloride, geranyl bromide and 2-(1'-methylcyclohexen-4'-yl)-2-propenyl bromide.

6. In the method of claim 3 wherein the reaction mixture from the alkylation step contains acid products of $C_{10}$ or less, the additional steps comprising:
   a. quenching the reaction mixture with water and removing precipitated copper salts;
   b. adjusting the reaction mixture to about pH 12 and removing additional precipitated copper salts;
   c. extracting the mixture with ether to remove non-acidic organic residues;
   d. acidifying the reaction mixture to about pH 3 and extracting the product acid with ether; and
   e. isolating the product acid by drying the ether extract and by evaporating the ether.

7. In the method of claim 3 wherein the reaction mixture from the alkylation step contains acid products of $C_{11}$–$C_{14}$, the additional steps comprising:
   a. quenching the alkylation reaction mixture with dilute hydrochloric acid and adjusting to about pH 3 and removing precipitated copper salts;
   b. extracting the product acid with ether; and
   c. isolating the product acid by drying the ether extract and removing ether by evaporation.

8. In the method of claim 3 wherein the reaction mixture from the alkylation step contains acid products of $C_{15}$ and higher, the additional steps comprising:
   a. quenching the alkylation reaction mixture with dilute hydrochloric acid and adding saturated ammonium chloride solution to dissolve all of the copper salts;
   b. extracting product acid with ether; and
   c. isolating the product acid by drying the ether extract and by removing ether by evaporation.

9. The method of synthesizing farnesoic acid comprising the steps of:
   a. forming the dicopper(I) dienolate of senecioic acid;
   b. selectively alkylating the dicopper(I) at the gamma position with geranyl bromide; and
   c. isolating farnesoic acid from the reaction mixture of step (b).

10. The method of synthesizing geranoic acid comprising the steps of:
   a. forming the dicopper(I) dienolate of senecioic acid;
   b. selectively alkylating the dicopper(I) dienolate at the gamma position with 3,3-dimethallyl bromide; and
   c. isolating geranoic acid from the reaction mixture of step (b).

11. The compound 2-(1'-penten-2'-yl)-4-penetenoic acid having the formula

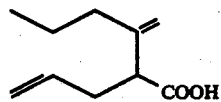

12. The compound 3-propyl-2,6-heptadienoic acid having the formula

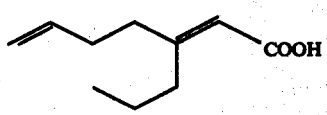

13. The compound 2,5-dimethyl-2-vinyl-4-hexenoic acid having the formula

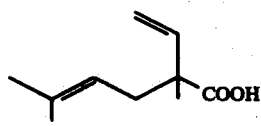

14. The compound (E)-2,5,6-trimethyl-2,6-heptadienoic acid having the formula

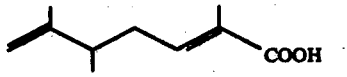

15. The compound (E,E)-2,6-dimethyl-2,6-octadienoic acid having the formula

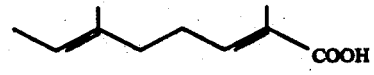

16. The compound (E,Z)-2,6-dimethyl-2,6-Octadienoic acid having the formula

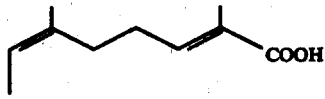

17. The compound (E,E)-2,6-dimethyl-2,6-undecadienoic acid having the formula

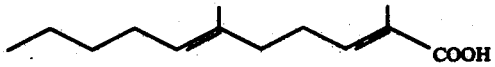

18. The compound 2,4-dimethyl-2-vinyl-4-pentenoic acid having the formula

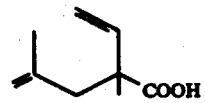

* * * * *